United States Patent [19]
Clark et al.

[11] Patent Number: 5,556,416
[45] Date of Patent: Sep. 17, 1996

[54] ENDOSCOPIC INSTRUMENT

[75] Inventors: George A. Clark, East Windsor, N.J.; Steven K. Heisel, Buffalo; Arlen L. Johnson, Plymouth, both of Minn.; Chris Robinson, Lawrenceville, N.J.; Mark K. Dana, Shorewood, Minn.

[73] Assignee: Valleylab, Inc., Boulder, Colo.

[21] Appl. No.: 134,560

[22] Filed: Oct. 12, 1993

[51] Int. Cl.⁶ .................................................. A61B 17/00
[52] U.S. Cl. ........................... 606/205; 606/170; 128/750
[58] Field of Search ................................... 606/205–210, 606/83, 174, 51, 52; 128/750–755; 81/319–324

[56] References Cited

U.S. PATENT DOCUMENTS

| | | |
|---|---|---|
| 3,895,636 | 7/1975 | Schmidt . |
| 4,703,560 | 11/1987 | Brooker . |
| 4,760,848 | 8/1988 | Hasson . |
| 4,982,727 | 1/1991 | Sato . |
| 5,160,343 | 11/1992 | Brancel . |
| 5,171,247 | 12/1992 | Hughett . |
| 5,171,256 | 12/1992 | Smith . |
| 5,171,258 | 12/1992 | Bales . |
| 5,176,702 | 1/1993 | Bales . |
| 5,201,759 | 4/1993 | Ferzli . |
| 5,211,655 | 5/1993 | Hasson ..................... 606/205 |
| 5,217,460 | 6/1993 | Knoepfler . |
| 5,219,357 | 6/1993 | Honkanen . |
| 5,234,460 | 8/1993 | Stouder . |

OTHER PUBLICATIONS

DaVinci Medical, "The DaVinci Line: Revolutionary Instruments for Laparoscopic Surgery", 1991.
Marlow Surgical Technologies, Inc., "Introducing the Primus Collection–the Flexibility to Create your own Instruments", 1991.
Stryker Endoscopy, "Instruments for Endoscopic Surgery".

*Primary Examiner*—Stephen C. Pellegrino
*Assistant Examiner*—William Lewis
*Attorney, Agent, or Firm*—Jones & Askew

[57] ABSTRACT

The improved endoscopic instrument of the present invention includes handles, a shaft and an end effectors. The handle is capable of adjustment to accommodate variations in hand size, and grip style. The handle is also adjustable relative to the shaft for use in a variety of medical procedures. In addition, the control linkages for the end effector of the improved endoscopic instrument of the present invention do not directly contact the patient thereby enabling the instrument to be easily cleaned, sterilized and reused.

16 Claims, 6 Drawing Sheets

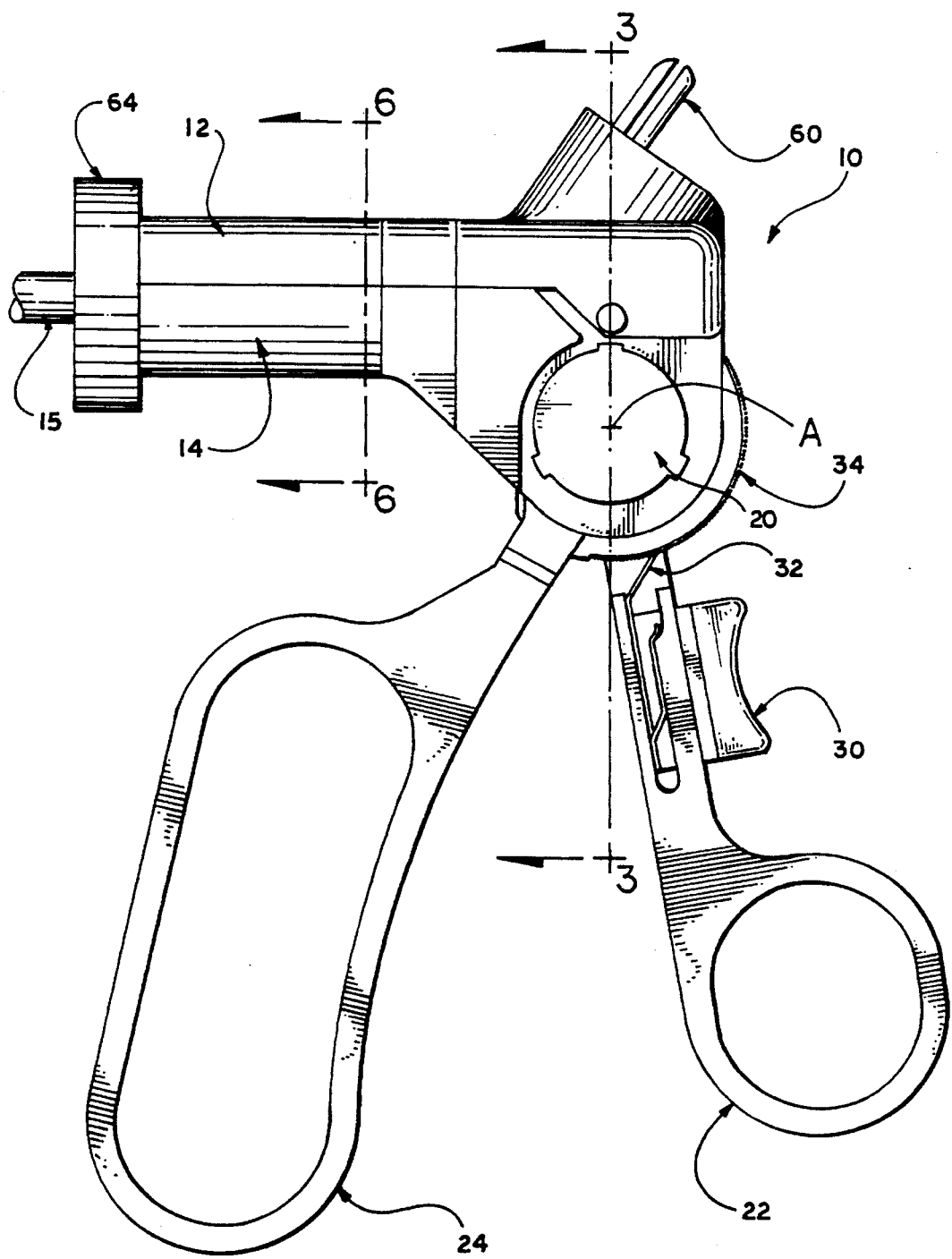
Fig_1

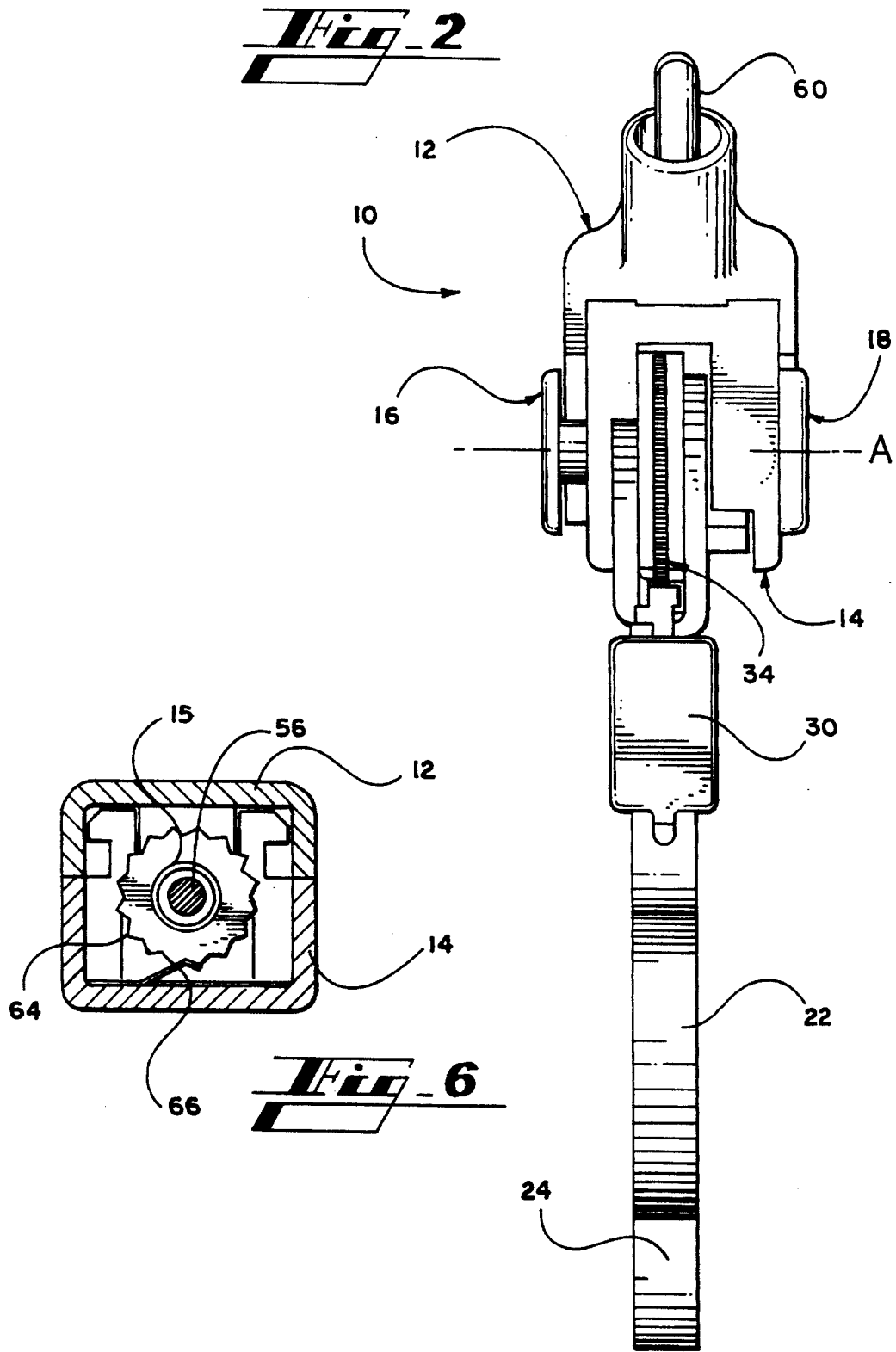

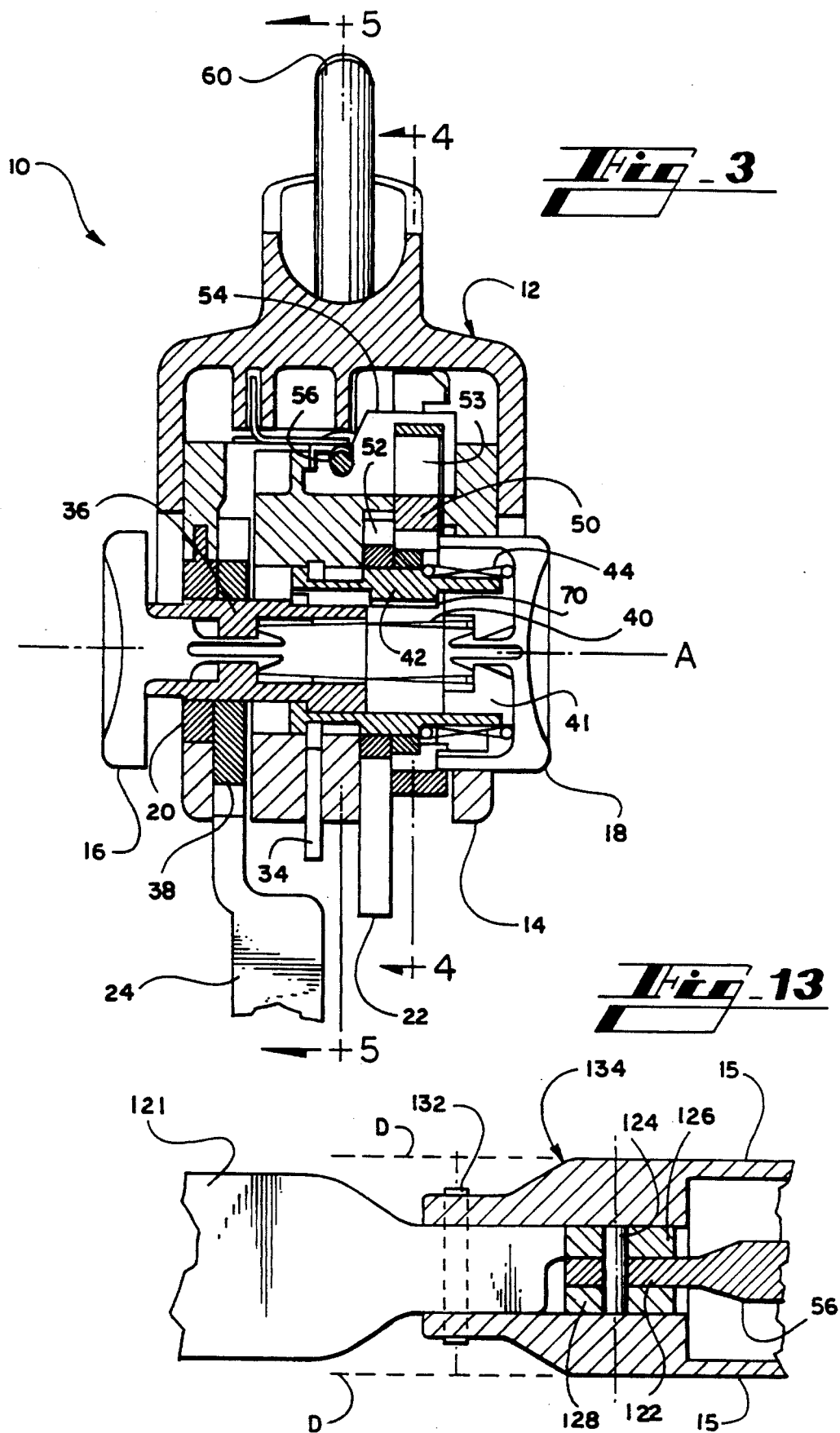

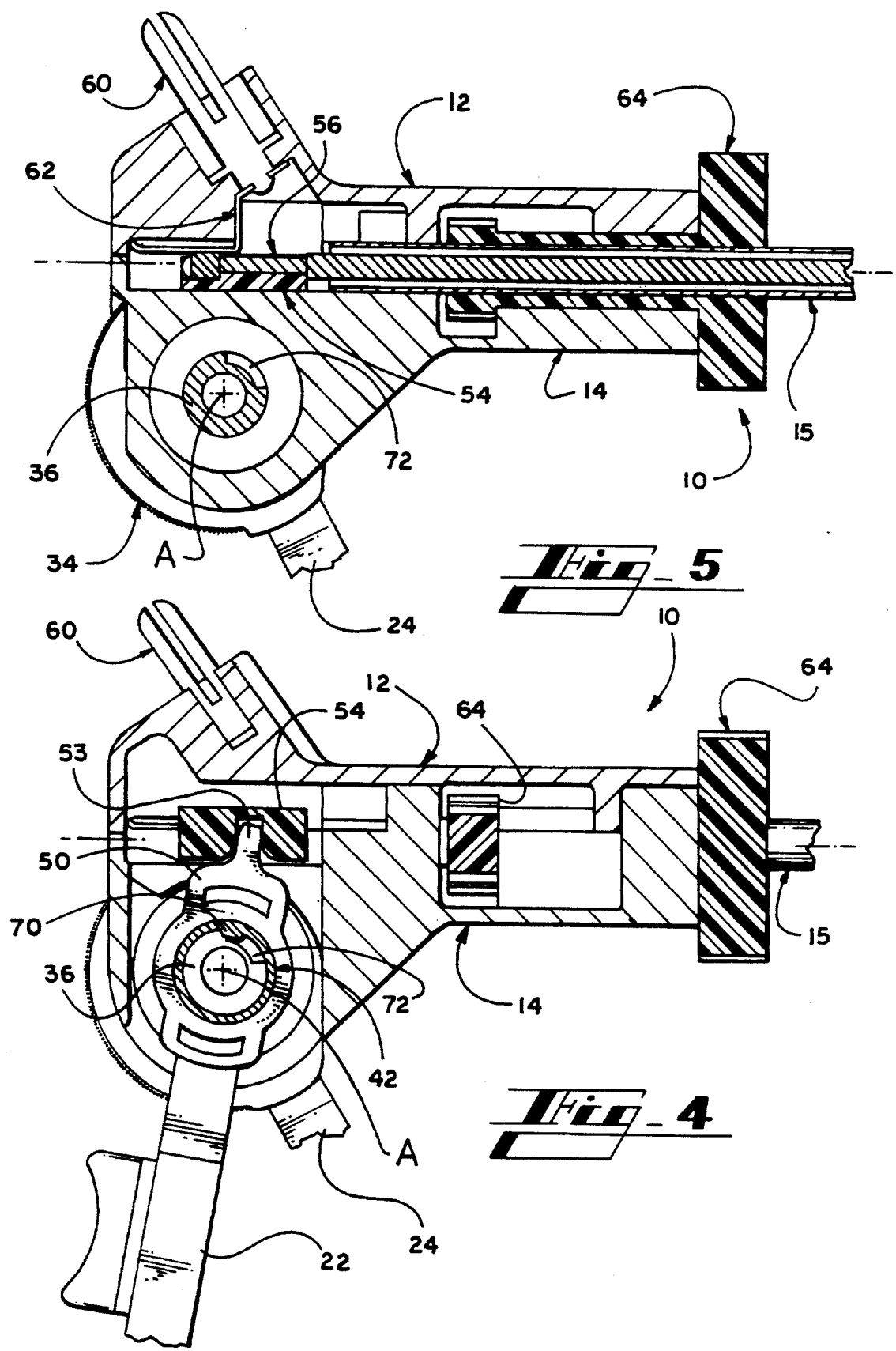

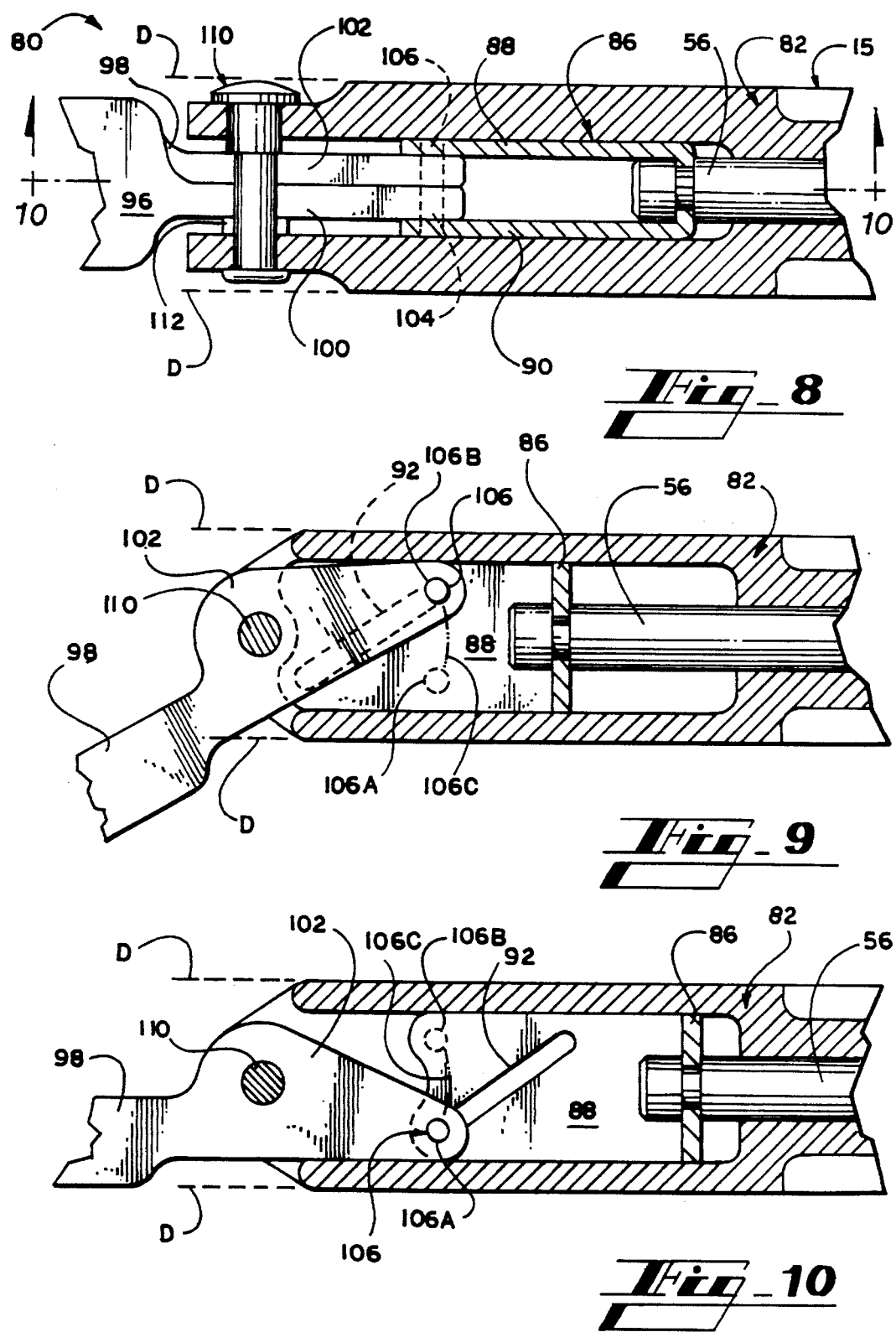

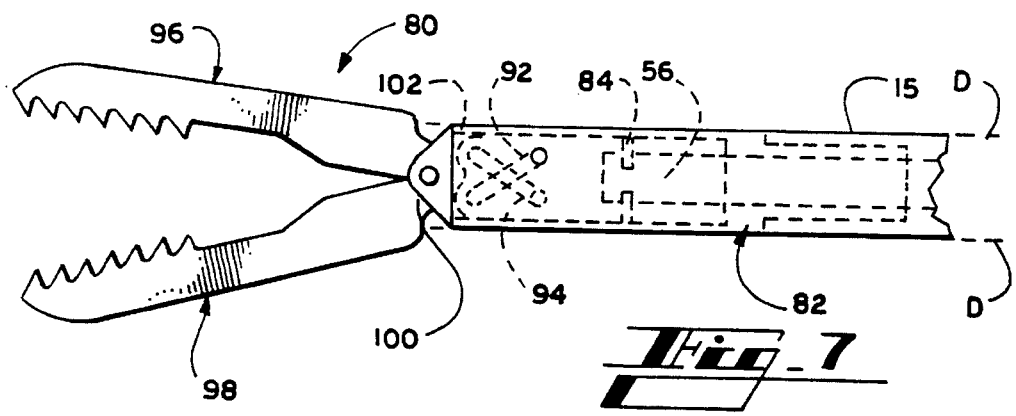
Fig_7
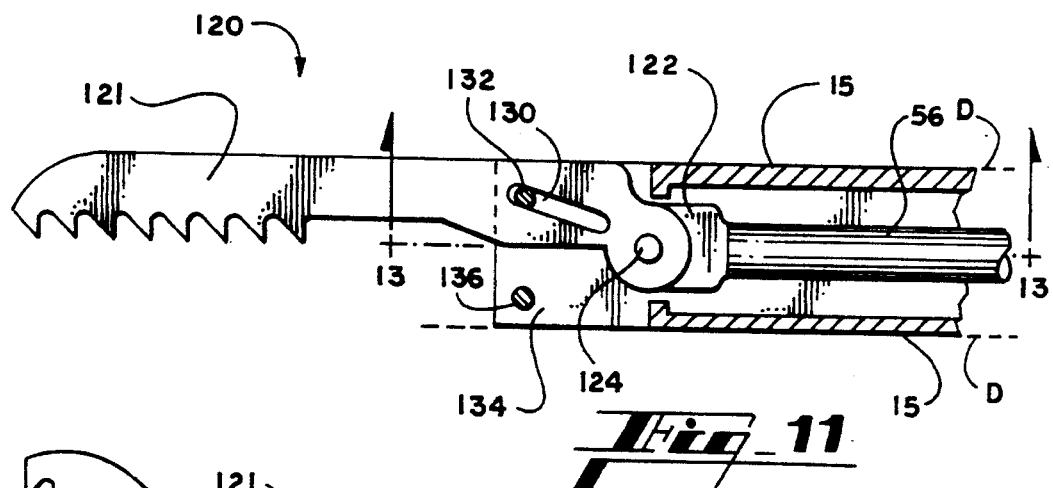
Fig_11
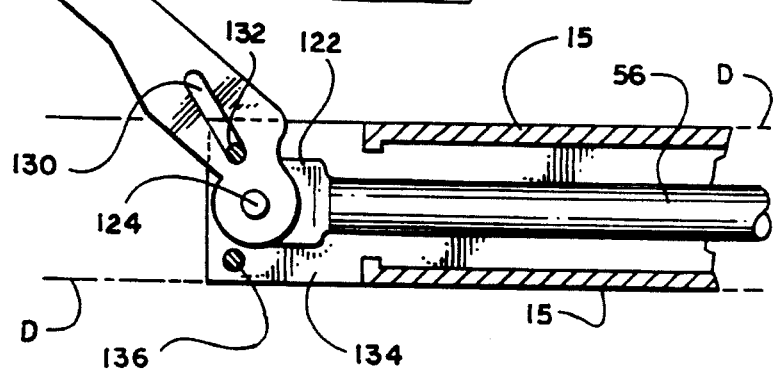
Fig_12

ENDOSCOPIC INSTRUMENT

TECHNICAL FIELD

The present invention relates generally to endoscopic instruments and relates more specifically to an improved endoscopic instrument that allows for adjustability of the handles to facilitate a variety of medical procedures, accommodates variations in hand span sizes and grip styles, and easily facilitates cleaning, sterilization and reuse.

BACKGROUND OF THE INVENTION

Endoscopic surgery has recently become a widely practiced surgical procedure. One type of endoscopic surgery, laparoscopic surgery, generally involves a small incision such as through the navel and abdominal wall to view or operate on organs or tissue located in the abdominal cavity. A camera or lens is placed in the area to aid the surgeon in guiding the endoscopic instrument to the particular area to be observed or operated upon.

Endoscopic instruments typically have a handle, an elongated shaft section and any one of a number of surgical tools attached to the shaft. The tools attached to the shaft are referred to as "end-effectors" and may include, for purposes of reference and not exclusion, needle holders, graspers, dissectors, cutters, and scissors. The movement of the end effectors are typically controlled at the proximal end of the instrument by manipulating the handle or a control mechanism located on the housing or the shaft.

At present, most handle portions of endoscopic instruments are shaped in one of two configurations. The first handle configuration closely resembles the handle of a pair of scissors. The handles are ring-shaped and are fixed to close and open relative to one another such that the end effectors may be properly manipulated. The ring-shaped handles do not provide for any adjustability for variations in hand and finger size. Because the surgeon must place his or her fingers through the handle rings, if the span of the surgeon's fingers is too small or too big to fit between the rings, the surgeon is unable to maintain a proper and comfortable grip on the instrument. A second configuration of the handle portion of endoscopic instruments resembles a pistol grip. This style handle has a portion extending downwardly from the shaft. However, this configuration does not provide for any adjustability for variations in hand sizes. A surgeon with a large hand may find it uncomfortable or cumbersome to properly grip the instrument. Conversely, a surgeon with small hands may not be able to adequately grasp the handle so as to properly hold and support the instrument.

Neither the scissors nor the pistol grip configurations adequately address the needs of surgeons who all have various hand sizes, and grip styles when conducting surgery. There is at present no handle on an endoscopic instrument that adjusts relative to itself to accommodate variations in hand sizes as well as variations in grip styles. Because all users of presently existing endoscopic instruments must grip them in the identical fashion, many surgeons develop cramps or discomfort in their hands or backs after holding the instrument for a period of time. In addition, many surgeons must be forced to grip the instrument in a manner that is uncomfortable to them. Thus, it would be advantageous to have an endoscopic instrument that has adjustable handles to accommodate variations in hand sizes, and grip styles.

In addition, there is no existing endoscopic instrument capable of adjusting tile position of the shaft relative to the handle to accommodate different surgical procedures. There are many surgical applications for an endoscopic instrument. There are four general categories of surgery in which an endoscopic instrument may be used. These include thoracic, general abdominal, urological and gynecological.

With each of these categories of surgery, the shaft is angled with respect to the handle in a different manner. For example, in hernia surgery, the endoscopic instrument used forms an acute angle between the handle and shaft. The acute angle between the shaft and handle enables the surgeon to maneuver the endoscopic instrument through the navel and down the front portion of the patient's abdomen just below the skin to operate. With respect to general abdominal surgery, it is often most desirable to have an endoscopic instrument that has the handles and shaft perpendicular to one another. In gynecological surgery and procedures, the shaft and handle should typically be 180° relative to one another.

As a result of different procedures, the preferred configuration of the endoscopic instruments used in each of these procedures is different. At present, a surgeon is apt to use a different endoscopic instrument for each of the procedures described above. This increases the cost of the surgery for the surgeon, the hospital, the insurance company and ultimately the patient. It would be beneficial for tile surgeon and all concerned to have a single instrument capable of adjusting the handles relative to the shaft that could be used for all surgical procedures described above. This would save surgeons, hospitals, insurance companies and consumers money on health care which continues to increase at a rate much higher than inflation.

Most prior art endoscopic instruments have end effectors that have moving parts such as hinges or linkages of some type. These end effector control linkages protrude from the body of the shaft when the end effector is controlled. This is undesirable because such protrusions tend to catch on tissue and cause unwanted damage. In addition, any deposits of tissue or bodily fluid in the linkage of the end effector make it difficult to clean, sterilize and reuse. It is desirable to have an endoscopic instrument that has end effectors that do not have any operating linkages that contact the patient. Such a feature would enable the end effector and instrument to be easily cleaned, sterilized and reused.

Thus, there is a need for an endoscopic instrument having handles that adjust to accommodate different hand sizes and different grip styles.

There is a further need for an endoscopic instrument having handles that adjust relative to the shaft for use in a variety of different medical procedures.

There is still a further need for an endoscopic instrument that enables the user to lock the jaws of the end-effector without maintaining pressure on the handles.

There is yet a further need for an endoscopic instrument where the operating linkages for the end effectors do not directly contact the patient.

There is an even further need for an endoscopic instrument that is cleanable sterilizeable and reusable.

SUMMARY OF THE INVENTION

As will be seen, the present invention overcomes these and other disadvantages associated with prior art endoscopic instruments. Stated generally, the present provides a handle for an endoscopic instrument, the handle defining an instrument shaft having an end-effector at its distal end. The handle of the invention includes a thumb handle for engaging at least a thumb of the user and a finger handle for engaging at least one of the other fingers of the user. At least one of the thumb handle and the finger handle is capable of at least partial rotation about a central axis of the handle such that when the instrument is in a normal orientation, movement of the thumb handle and finger handle toward one another moves the end-effector toward a first orientation and movement of the thumb handle and finger handle away from one another moves the end-effector toward a second orientation. A first disengagement mechanism is provided which is configured to release the thumb handle or finger handle and allows for arrangement of the thumb handle about the central axis independent of the movement of the end-effector. The disengagement mechanism works such that when the mechanism is operated, the distance between the thumb handle and the finger handle may be adjusted to fit the hand of the user. A second disengagement mechanism may be provided which allows the thumb handle and finger handle to be rotated about the axis such that they may be arranged relative to the shaft so that an optimal angle may be established between the shaft and the handles.

The present invention is also directed to an end-effector for the tool handle. The end-effector includes a surgical tool which is capable of a first orientation and a second orientation. In addition, the end-effector includes a camming surface or a cam, said camming surface set for engaging the cam. One of the cam and the camming surface is fixed relative to the shaft of the tool, and the other of the cam and the camming surface is fixed for movement with the rod actuator. The end-effector works such that axial movement of the rod actuator in the shaft causes the surgical tool to move from the first orientation to the second orientation. During this movement, the cam remains within the outer wall of the shaft during the movement.

Accordingly it is an object of the present invention to provide an endoscopic instrument that has handles that adjust to accommodate different hand sizes and different grip styles.

It is a further object of the present invention to provide an endoscopic instrument that has handles that adjust relative to the shaft for use in a variety of different medical procedures.

It is still a further object of the present invention to provide an endoscopic instrument where the operating linkages for the end effectors do not directly contact the patient.

It is still a further object of the present invention to provide an endoscopic instrument that is cleanable, sterilizeable and reusable.

These and other objects, features and advantages of the present invention will become apparent upon reading the following detailed description of the preferred embodiment of the invention, when taken in conjunction with the drawings and appended claims.

BRIEF DESCRIPTION OF THE DRAWINGS

The invention will now be described with reference to the accompanying drawings which illustrate a preferred embodiment of the endoscopic instrument, falling within the scope of the appended claims, and in which:

FIG. 1 is a side view of a reconfigurable endoscopic tool handle in accordance with the present invention.

FIG. 2 is a rear view of the handle of FIG. 1.

FIG. 3 is a cut-away perspective along the lines 3—3 in FIG. 1.

FIG. 4 is a cut-away perspective along the lines 4—4 in FIG. 3.

FIG. 5 is a cut-away perspective along the lines 5—5 in FIG. 3.

FIG. 6 is a cut-away perspective along the lines 6—6 in FIG. 1.

FIG. 7 is a side view of an end-effector embodying the end-effector of the present invention.

FIG. 8 is a top view of the end-effector of FIG. 7, with part of the insert for the shaft removed.

FIG. 9 is a side view of the end-effector of FIG. 7 taken along the line 10—10 in FIG. 8, showing the grasper arm in an open orientation.

FIG. 10 is a side view of the end-effector of claim 9, showing the grasper arm in a closed configuration.

FIG. 11 is a cutaway perspective view of a second embodiment of an end-effector of the present invention, the perspective view showing one of the grasper arms and having a second of the grasper arms removed.

FIG. 12 is the end-effector of FIG. 11, with the grasper arm in the open position and the actuator rod advanced in the shaft.

FIG. 13 is a cutaway perspective view of the end-effector of FIG. 11 taken along the lines 13—13.

DETAILED DESCRIPTION OF THE INVENTION

Referring now to the drawing, in which like reference numerals represent like parts throughout the several views, FIG. 1 depicts a reconfigurable endoscopic tool handle 10 in accordance with the present invention. The tool handle 10 has a central axis A therethrough and includes a removable housing top 12 and a housing bottom 14. A shaft 15 of the tool, onto which surgical tools or end effectors are attached, extends through the handle 10 and out of the distal end. The central axis A extends substantially perpendicular to this shaft 15.

As can best be seen by FIG. 2, the handle 10 includes a left button 16 and a right button 18 at the rear portion of the housing bottom 14. The left button 16 is removed in FIG. 1 so that a splined insert 20 may be seen.

The handle 10 preferably includes a thumb handle 22 for engaging at least the thumb of a user, and a finger handle 24 for engaging at least one of the fingers of the hand of the user. The thumb handle 22 includes a ratchet slide switch 30 which is connected to a ratchet pawl 32. The ratchet pawl 32 engages separate teeth of a ratchet plate 34, as is described in detail below.

The working relationship between the thumb and finger handles 22, 24 and the buttons 16, 18 is best described by reference to FIG. 3. The left button 16 is preferably a hardened plastic and includes a snap-end which is received in a hole in a splined shaft 36. When the left button 16 is in a normal orientation (i.e., not depressed) the splines in this shaft 36 engage both the splines in the insert 20 in the housing bottom 14 and the splines in an insert 38 in the top end of the finger handle 24. The shaft 36 includes a narrowed, smooth surface between the splines and the left button 16, the use of which will be described below. A spring 40 is journaled within and extends out of the right end of the splined shaft 36 to resist movement of the splined shaft 36 and the left button 16 inward in the housing. The other end of the spring 40 is journaled in a cylinder end cap 41.

The right button 18 includes a snap-end, which is received in a hole in the cylinder end cap 41. The cylinder end cap 41 is attached to a splined cylinder 42. The splined cylinder 42 is larger in diameter than and is configured to receive the right end of the splined shaft 36. A spring 44 engages the inner portion of the button 18 for resisting movement of the button 18 and cylinder 42 inward relative the housing.

Moving from the button end of the cylinder 42 toward the right end of the cylinder, the splined portion of the cylinder 42 engages first a rocker arm 50 having splines therein and then a splined insert 52 for the thumb handle 22. The cylinder 42 includes a narrowed, smooth surface between the splines and the button 18, the purpose of which will be described below.

As can best be seen in FIG. 4, the end of the rocker arm 50 includes a camming surface 53 which has the appearance of finger and which is set to engage an actuator rod cradle 54. This cradle 54 includes an inset for receiving an actuator rod 56 from one of many endoscopic instruments. The actuator rod 56 extends through the shaft 15 of the instrument to an end-effector or surgical tool. The shaft 15 extends through the handle 10 and out of the distal end, as is best shown in FIGS. 5 and 1. Also included in the housing top 12 is an electrical jack pin 60 and an electrical contact 62 for use in electro cautery applications.

As is shown in FIG. 6, the shaft 15 includes a one-piece gear and rotation knob 64 fixed for rotation with the shaft. By rotating this knob 64, tile shaft 15 and actuator rod 56 are also rotated. In turn, the end-effector may be rotated to desired orientation. This rotation does not affect the internal mechanism of the housing or its ability to transfer motion to the actuator rod 56, because tile actuator rod 56 is free to rotate within the actuator rod cradle 54. The gear of the knob 64 contacts a spring detent 66 to hold the rod 56 and end effector in place after rotation.

The manner in which operation of the reconfigurable endoscope tool handle 10 works is understood from the above description. In use, a surgeon or any other user opens the housing top 12 of the tool handle 10 and places a selected shaft 15 having an end-effector (not shown) in the tool. The shaft 15 of the tool includes the one-piece gear and rotation knob 64 and is oriented such that it extends out of the distal end of the tool handle 10 and the actuator rod 56 fits into the actuator rod cradle 54.

The housing top 12 is then replaced and the tool handle 10 is now ready for use. The surgeon simply places his or her fingers into the finger handle 24 and his or her thumb into the thumb handle 22. By gripping the thumb handle 22 toward the finger handle 24, the doctor causes a series of events to occur. Because both the splined insert 20 on the housing 14 and the splined insert 38 for the finger handle 24 are located on the splines of the shaft 36, the finger handle 24 remains fixed relative to the housing 14. The thumb handle 22, on the other hand, is located on the splines of the cylinder 42 along with and adjacent to the rocker arm 50. The splined cylinder 42 is not fixed with the housing, but instead is free to rotate about the central axis A of the tool handle 10. Therefore, movement of the thumb handle 22 back and forth relative to the finger handle 24 causes the rocker arm 50 to move back and forth within the housing. As can be appreciated by FIG. 4, this movement of the rocker arm 50 back and forth causes the camming surface 53 to engage the actuator rod cradle 54 to move the cradle in a linear manner back and forth in the housing. This movement results in the actuator rod 56 moving in and out of the shaft 15, allowing the end-effector to change from a first orientation to a second orientation. If the end-effector is of the grasper type, such as known in the industry, such movement may open and close the jaws of the grasper.

The movement of the thumb handle 22 in one direction may be prevented by use of the ratchet slide switch 30. In FIG. 1, the ratchet slide switch 30 is engaged such that the ratchet pawl 32 is inserted between two teeth of the ratchet plate 34. The angle of the ratchet pawl 32 is such that when tile thumb handle 22 is pressed toward the finger handle 24, the ratchet pawl 32 bends slightly and clicks into the space between the next pair of ratchet teeth. However, movement of the thumb handle in the reverse direction is prevented because the angle of the pawl 32 causes the end of the pawl to dig into the set of teeth on the ratchet plate 34 instead of clicking over the teeth.

The use of the ratchet pawl 32 causes movement of the thumb handle 22 towards the finger handle 24 to occur in incremental steps, in between which no pressure need be applied by the user to the handles. The pawl 32 is also useful for locking the position of the thumb handle 22 relative to the finger handle 24. In this manner. The end-effector may be held in the closed position without it being necessary for the surgeon to keep his or her hand on or apply pressure to the thumb handle 22 or finger handle 24. The end-effector and the thumb handle 24 may be released by simply sliding the ratchet slide switch 30 toward the ring for receiving a thumb on the thumb handle. This removes the pawl 32 from the ratchet plate 34 and allows free movement of the thumb handle 22 in either direction.

The thumb handle 22 and the finger handle 24 may be adjusted relative to one another and about the central axis A of the tool handle 10 by use of one or more release mechanisms. These release mechanisms are provided in the embodiment shown in the drawing by the left and right buttons 16, 18 and the internal mechanisms connected to the buttons and displayed in FIG. 3.

Rotation of the finger handle 24 about the central axis A is made possible by simply depressing the left button 16 against the force of tile spring 40 until the splined portion of the shaft 36 extends inward past the housing insert 20. This allows the smooth, outer portion of the splined shaft 36 to be adjacent to the housing insert 20 and keeps the splines of the shaft 36 in contact with the splined insert 38 for the finger handle 24. Because the housing insert 20 is no longer in contact with the splines of the splined shaft 36, the finger handle 24 may be rotated with the shaft 36 about the axis A to a desired orientation. The left button 16 is then released and the spring 40 returns the button 16 back to its original orientation. In the course of this movement, the splines of the shaft 36 are reinserted into the housing insert 20 and the finger handle 24 is locked once more into place relative to the housing.

Likewise, the thumb handle 22 may be rotated about the central axis A by depressing the right button 18 against the spring 44. Depressing the right button 18 causes the spring 44 to compress and the splined cylinder 42 to move toward the left button 16. This movement causes the splined portion of the cylinder 42 to move from underneath the rocker arm 50 so that the smoother, narrower portion of the cylinder extends under the rocker arm. However, the splines of the cylinder 42 remain engaged with the splined insert 52 for the thumb handle 22. The thumb handle 22 and the splined cylinder 42 may then be rotated about the axis A while the rocker arm 50 remains in place.

For purposes of safety, the thumb and finger handles 22, 24 should not be over-rotated or under-rotated relative to one another, or it may be impossible for a surgeon to open or close the end-effector. This may happen one of two ways. The handles 22, 24 may be too far apart for the surgeon to spread them by simply fanning his or her hand open, or the handles may be so close together that they touch and do not allow full range of movement so that the end-effector may be closed. The present inventors have found that most users have an effective range of movement of the handles between approximately 0° to 70°. That is, most users can close the handles so that they touch completely (a 0° gap) or open them to an orientation of 70° from one another (a 70° gap). However, for complete movement of the rocker arm 50 and therefore the actuator rod 56 and the end-effector, there must be 20° of full movement in the handles. This means that the 20° of movement should fall somewhere in the comfortable range of the user, or within the approximately 0° to 70° gap. Therefore, for optimal use of the tool the handles 22, 24 should never be adjusted less than 20° apart (the minimum distance between the handles for a user or 0°, plus the additional 20° needed for full movement) or more than 50° apart (the maximum separation the handles, or 70°, minus the needed movement of 20°). This allows full movement of the handles 22, 24 by a user in either direction after adjustment has been made.

To prevent this over- or under-adjustment of the handles relative to one another, a tab 70 is provided on the inside of the splined cylinder 42, as is shown in FIG. 4. This tab 70 is configured for cooperating with a narrowed portion 72 of the splined shaft 36. The tab 70 and the narrowed portion 72 work together as a stop to prevent rotation of the handles 22, 24 relative one another outside the comfortable range of motion of a hand of the user. As can be appreciated by FIG. 3, as long as the buttons 16, 18 are not depressed, rotation of the splined cylinder 42 is unimpeded by the splined shaft 36. This is because the tab 70 falls short of the right end of the splined shaft 36 when the buttons 16, 18 are at an arrest position. However, if insertion of the left button 16, the right button 18, or both is attempted, that insertion will not be possible unless the tab 70 aligns along one part of the narrowed portion 72 of the splined shaft 36. The area in which the tab 70 may be inserted into the narrow portion 72 represents an allowable range of movement in which the buttons 16, 18 can be inserted and corresponds to the handles being 20° to 50° apart, the significance of which was discussed above. Likewise, while one or both of the buttons 16, 18 is inserted. The tab prevents over-rotation of one of the handles 22, 24 relative to the other. In this manner, the handles 22, 24 are always in a workable position after repositioning of one or both of the handles.

By use of the buttons 16, 18 and the mechanisms attached to them, the finger and thumb handles 24, 22 may be rotated about the central axis A and relative to the tool 10 so that an advantageous angle may be formed between the shaft 15 and the handles. This allows the handles 24, 22 to be used for thoracic, general abdominal, urological, and gynecological surgeries. By pushing both of the buttons 16, 18 in at once, it is possible to move the finger and thumb handles 24, 22 in unison and to place them in a desired orientation. This gives the surgeon a single instrument capable of many orientations of the handles 24, 22 relative to the shaft 15 so that the tool handle 10 could be used for numerous surgical procedures. Moreover, by pressing in one or both of the buttons 16, 18 on the tool 10, the handles 22, 24 may be adjusted relative to one another so that the handles may fit any size hand.

The tool handle 10 may be used with a variety of different end-effectors, including but not limited to needle holders, graspers, disectors, cutters, and scissors. The end-effectors are operated by the movement of the actuator rod 56 within the shaft 15. This relative movement can cause a grasper jaw to open and close, a cutter blade to cut and retract, or a needle holder to grasp or let go of a needle.

The unique design of the tool handle 10 allows it to be universal for all types of end-effectors. The cradle 54 offers a linear motion which can either be back and forth, or forward in one direction and held in that position for as long as needed. The actuator rod 56 is keyed for precise fitting into that cradle 54 and moves along with the cradle. The shaft 15, on the other hand, is fixed to prevent axial movement in and out of the tool. The shaft 15 and rod 56 may be rotated by use of the rotation knob 64 which allows full 360° rotation of the end-effectors for precise alignment of the end-effector, which enables efficient operator control and eliminates awkward wrist movements.

An example of an end-effector 80 which may be used with the tool handle 10 is pictured in FIG. 7. The end-effector 80 is of the grasper variety. The embodiment shown in FIG. 7 provides operating linkages which remain within the outer diameter D of the shaft 15 and therefore the linkages do not contact the patient during rise.

As can be seen by FIG. 7, the distal end of the shaft 15 includes an insert 82 extending the same diameter as the shaft to the end-effector 80. The actuator rod 56 extends through the shaft 15 and the insert 82. A groove 84 in the annular rod is set to receive a U-shaped plate 86. The U-shaped plate 86 extends up the insert 82 such that opposite sides 88, 90 (shown in FIG. 8) of the U-shaped plate face one another. FIG. 8 is a top side view of the end-effector 80 shown in FIG. 7 and has part of the insert 82 removed so that the relation of the plate 86 to the rod 56 and other internal mechanisms may be shown.

The inner surface of each side of the plates 88, 90 include camming surfaces in the form of cam slots 92, 94. A first of the cam slots 92 extends diagonally from a lower, distal portion of the rear plate 88 to a higher, central portion of the plate. The second cam slot 94 extends diagonally from the upper, distal end of the internal portion of the plate 90 to a lower, central portion of the plate. Thus, if it were possible to peer through the insert 82, the two cam slots would seem to cross and form an "x" as is shown in FIG. 7.

The grasper shown in FIG. 7 includes two grasper arms 96, 98. Each of these arms includes a flat, triangular section 100, 102 which partially extends into the insert 82. Cams in the form of pins 104. 106 are included in the ends of the flat, triangular sections 100, 102 for engaging the cam slots 94, 92. A stationary pin 110 extends through each of the grasper arms 96, 98 at the distal end of the insert 82. The stationary pin 110 acts as a fulcrum about which the grasper arms 96, 98 can rotate. Rubber gaskets 112 (only one shown) are included on opposite sides of the two triangular plates 100, 102 to allow free movement of tile grasper arms 96, 98 about the pin 110.

FIGS. 9 and 10 are provided to better describe the operation of the end-effector 80. FIG. 10 is a cross-section along the hatch lines 10—10 of FIG. 8 and for the purposes of clarity has the grasper arm 96 removed. FIG. 9 is the same cross-section as FIG. 10, but has the annular rod 56 advanced in the shaft 15 and the insert 82.

The manner in which the end-effector 80 operates is apparent from the above description and the drawings provided in FIGS. 9 and 10. The grasper arm 98 is shown in the closed position in FIG. 10 with the pin 106 located at the distal end of the cam slot 92 in the position 106A. As the actuator rod 56 is advanced in the shaft 15 and the insert 82, the pin 106 correspondingly advances upward in the cam slot 92. As the actuator rod reaches the end of its advancement, the pin 106 reaches the position 106B and the grasper arm 98 is in the open position. During movement of the actuator rod 56, the pin 106 travels along the path 106C.

As can be understood from the above description, the end-effector 80 utilizes the linear motion of the actuator rod 56 to create first and second orientations of the grasper (closed and opened positions). The movement changes of the end-effector 80 are accomplished without control linkages protruding from the outer diameter D of the shaft. Thus, there are no provisions to catch on tissue or other body parts to cause unwanted damage.

A second end-effector 120 having many of these same characteristics is pictured in FIG. 11. Like the end-effector 80, the end-effector 120 pictured in FIG. 11 is of the grasper variety and is driven by linear, back-and-forth movement of the actuator rod 56 within the shaft 15. A grasper arm 121 is shown in FIG. 11, and a second grasper arm (not pictured) is similarly mounted on the other side of the end-effector 120, as will be understood in the description below. The second grasper arm is removed in FIGS. 11 and 12 to facilitate understanding of the operation of the end-effector 120.

The rod 56 in the embodiment shown in FIG. 11 flattens out at its distal end into a flat piece 122. As can be seen in FIG. 13, a pin 124 extends through the flat piece 122 and also through two grasper arm extensions 126, 128. This pin serves as a pivot point for the two grasper arms. The grasper arm extension 126 is attached to the grasper arm 121 and the grasper arm extension 128 is attached to the second grasper arm (not pictured). The grasper arm 121 includes a camming surface in the form of cam slot 130 for engaging a cam in the form of it pin 132. As can be seen best by FIG. 13, the pin 132 extends through an extension 134 of the shaft 15, its well as the cam slot 130. A similar pin 136 is located on the other side of the extension 134 for engaging a cam slot in the second grasper arm (not shown).

The manner in which the end-effector 120 works can be appreciated from the above description and the drawings. In FIG. 11, the grasper arm 121 is in the closed position and the actuator rod 56 is in a retracted position. In FIG. 12, the actuator rod 56 has moved forward (or to the left in the drawing) causing the cam slot 130 to move forward and upward as a result of engagement with the pin 132. This forward and upward movement of the cam slot 130 causes a corresponding opening of the grasper arm 121. Retraction of the actuator rod 56 causes the grasper arm 121 to move backward and downward along the pin 132 until the grasper arm is back into the closed position.

As with the end-effector 80, the end-effector 120 utilizes the linear motion of the actuator rod 56 to create first and second orientations of the grasper pieces (closed and opened positions). The movement changes of the end-effector 120 are accomplished without controlling surfaces protruding from the outer diameter D of the shaft, and therefore the end-effectors do not cause damage to outlying tissue and can be easily cleaned, sterilized, and reused.

It should be understood that numerous modifications or alternations may be made to the device without departing from the spirit and scope of the invention as set forth in the appended claims.

What is claimed:

1. An endoscopic instrument comprising:
   a. a housing with a central axis extending there through;
   b. an instrument shaft extending from said housing;
   c. an actuator mounted for sliding movement along said instrument shaft;
   d. an end effector located at an end of said instrument shaft and connected to said actuator such that the end effector is selectively operable to first and second orientations by movement of said actuator relative to said instrument shaft;
   e. a thumb handle mounted for rotation about said central axis and extending at least partly into said housing and configured for engaging at least the thumb of a user;
   f. a finger handle mounted for rotation about said central axis and extending at least partly into said housing and configured for engaging at least one of the other fingers of the user;
   g. a rocker arm for engaging said actuator and mounted for rotation about said central axis;
   h. a first lock and release mechanism for selectively connecting a first of said thumb handle and said finger handle with said rocker arm, such that said first lock and release mechanism is selectively operable to release and lock positions, such that when said first lock and release mechanism connects said first handle to said rocker arm and said first look and release mechanism is in said lock position, said first handle rotates about said central axis relative to said housing with said rocker arm whereby said movement of said first handle relative to said housing causes said rocker arm to engage said actuator and thereby move said end effector from said first orientation toward said second orientation and, when said first lock and release mechanism is in said release position such that said first handle is not connected to said rocker arm, said first handle may rotate about said central axis relative to said housing independent of said rocker arm; and
   i. a second lock and release mechanism for selectively connecting said second of said thumb handle and said finger handle with said housing such that said second lock and release mechanism is selectively operable to release and lock positions which, when said second lock and release mechanism connects said second handle to said housing and said first lock and release mechanism in the lock position, said second handle is fixed to rotate with said housing, and when said second lock and release mechanism is in the release position such that said second handle is not connected to said housing, said second handle is free to rotate about said central axis relative to said housing.

2. The endoscopic instrument of claim 1, wherein said second handle is said finger handle and said first handle is said thumb handle.

3. The endoscopic instrument of claim 1, further comprising a stop configured for selective engagement with at least one of said finger handle and said thumb handle and which prevents rotation of said handles outside of a specified range when at least one of said lock and release mechanisms is in its respective release position.

4. The endoscopic instrument of claim 3, wherein said specified range is from approximately 20° to approximately 50°.

5. The endoscopic instrument of claim 3, wherein said stop is configured for selective engagement with at least one of said first and second release and lock mechanisms such that said stop prevents engagement of either of said release and lock mechanisms when said angle is outside of said specified range.

6. The endoscopic instrument of claim 5, wherein said specified range is from approximately 20° to approximately 50°.

7. The endoscopic instrument of claim 1, wherein said first lock and release mechanism further comprises a splined cylinder having a splined portion and a rounded portion, and wherein said first handle comprises a splined insert, said splined insert configured to receive said splined portion of said cylinder.

8. The endoscopic instrument of claim 7, wherein said rocker arm defines a splined insert therein, said insert in said rocker arm for receiving said splined portion of said cylinder, one of said splined insert on said rocker arm and said splined insert on said first handle being selectively positionable against the splined portion and the rounded portion of said splined cylinder.

9. The endoscopic instrument of claim 8, wherein said second lock and release mechanism further comprises a splined shaft having a splined portion and a rounded portion, and a splined insert on said housing for engaging the splined portion on said splined shaft, and wherein said second handle includes a splined insert for engaging the splined portion on said splined shaft; one of said splined insert on said housing and said splined insert on said second handle being selectively positionable against the splined portion and the rounded portion of said splined shaft.

10. The endoscopic instrument of claim 9, wherein said splined shaft is received within said splined cylinder.

11. The endoscopic instrument of claim 1, wherein said second lock and release mechanism further comprises a splined shaft having a splined portion and a rounded portion, and a splined insert on said housing for engaging the splined portion on said splined shaft, and wherein said second handle includes a splined insert for engaging the splined portion on said splined shaft; one of said splined insert on said housing and said splined insert on said second handle being selectively positionable against the splined portion and the rounded portion of said splined shaft.

12. The endoscopic instrument of claim 11, further comprising a stop located on one of the inside of said splined cylinder and the outside of said splined shaft, and a groove located on the other of the inside of said splined cylinder and the outside of said splined shaft, said stop configured to engage said groove and thereby prevent rotation of said handles outside of a specified range when at least one of said lock and release mechanisms is in its respective release position.

13. The endoscopic instrument of claim 12, wherein said specified range is from approximately 20° to approximately 50°.

14. The endoscopic instrument of claim 12, wherein said stop is configured to prevent engagement of either of said release and lock mechanisms into the respective release positions when said angle is outside said specified range.

15. The endoscopic instrument of claim 14, wherein said specified range is from approximately 20° to approximately 50°.

16. An endoscopic instrument comprising:

a. a housing with a central axis extending there through;

b. an instrument shaft extending from said housing;

c. an actuator mounted for sliding movement along said instrument shaft;

d. an end effector located at an end of said instrument shaft and connected to said actuator such that the end effector is selectively operable to first and second orientations by movement of said actuator relative to said instrument shaft;

e. a thumb handle mounted for rotation about said central axis and extending at least partly into said housing and configured for engaging at least the thumb of a user;

f. a finger handle mounted for rotation about said central axis extending at least partly into said housing and configured for engaging at least one of the other fingers of the user;

g. a rocker arm for engaging said actuator and mounted for rotation about said central axis, one of said thumb handle and said finger handle capable of rotation with said rocker arm, the other of said thumb handle and said finger handle capable of being fixed relative to said housing;

h. a first lock and release mechanism for selectively connecting one of said thumb handle and said finger handle with said rocker arm such that said mechanism is selectively operable to release and lock positions, such that when said first lock and release mechanism is in said lock position such that said one handle is connected to said rocker arm, said one handle is capable of at least partial rotation about said central axis with said rocker arm and relative to said housing and said movement of said one handle relative to the other of said thumb and finger handles causes said rocker arm to engage said actuator and thereby moves said end effector from said first orientation toward said second orientation and, when said first lock and release mechanism is in said release position, said one handle may rotate about said central axis relative to said other handle independent of said rocker arm and thereby independent of said movement of said end effector.

* * * * *